United States Patent
Larsen

(10) Patent No.: US 7,771,658 B2
(45) Date of Patent: Aug. 10, 2010

(54) DISPOSABLE CARTRIDGE FOR CHARACTERIZING PARTICLES SUSPENDED IN A LIQUID

(75) Inventor: Ulrik Darling Larsen, Holte (DK)

(73) Assignee: Chempaq A/S, Copenhagen O (DK)

( * ) Notice: Subject to any disclaimer, the term of this patent is extended or adjusted under 35 U.S.C. 154(b) by 1040 days.

(21) Appl. No.: 10/517,385

(22) PCT Filed: Jun. 11, 2003

(86) PCT No.: PCT/DK03/00385

§ 371 (c)(1),
(2), (4) Date: Jun. 27, 2005

(87) PCT Pub. No.: WO03/104772

PCT Pub. Date: Dec. 18, 2003

(65) Prior Publication Data

US 2006/0013725 A1    Jan. 19, 2006

Related U.S. Application Data

(60) Provisional application No. 60/387,407, filed on Jun. 11, 2002.

(30) Foreign Application Priority Data

Feb. 5, 2003    (DK) .............................. 2003 00159

(51) Int. Cl.
*G01N 15/10* (2006.01)
*G01N 15/12* (2006.01)

(52) U.S. Cl. ............... 422/82.01; 422/68.1; 422/98; 422/99; 422/102; 422/81; 436/52; 436/63; 436/179; 436/180; 73/863.71; 73/863.72; 73/864.63; 73/864.21; 321/71.1

(58) Field of Classification Search ............ 422/99, 422/102–104, 68.1, 73, 81, 100; 324/71.1, 324/71.4; 73/865.5, 61.71, 863.71, 863.72, 73/864, 864.11, 864.21, 864.63; 436/179, 436/180

See application file for complete search history.

(56) References Cited

U.S. PATENT DOCUMENTS 2,656,508 A    10/1953 Coulter (Continued)

FOREIGN PATENT DOCUMENTS

EP    0193394 B1    7/1991

(Continued)

OTHER PUBLICATIONS

Volker Kachel, "Electrical Resistance Pulse Sizing: Coulter-Sizing", Flow Cytometry and Sorting, pp. 45-80, 2nd ed., 1990 Wiley-Liss Inc.

(Continued)

*Primary Examiner*—Jill Warden
*Assistant Examiner*—Cedric Chan
(74) *Attorney, Agent, or Firm*—Volentine & Whitt, P.L.L.C.

(57) ABSTRACT

A disposable cartridge for characterizing particles suspended in a liquid, especially a self-contained disposable cartridge for single-use analysis, such as for single-use analysis of a small quantity of whole blood. The self-contained disposable cartridge facilitates a straightforward testing procedure, which can be performed by most people without any particular education. Furthermore, the apparatus used to perform the test on the cartridge is simple, maintenance free, and portable.

35 Claims, 12 Drawing Sheets

U.S. PATENT DOCUMENTS

Figure 1:
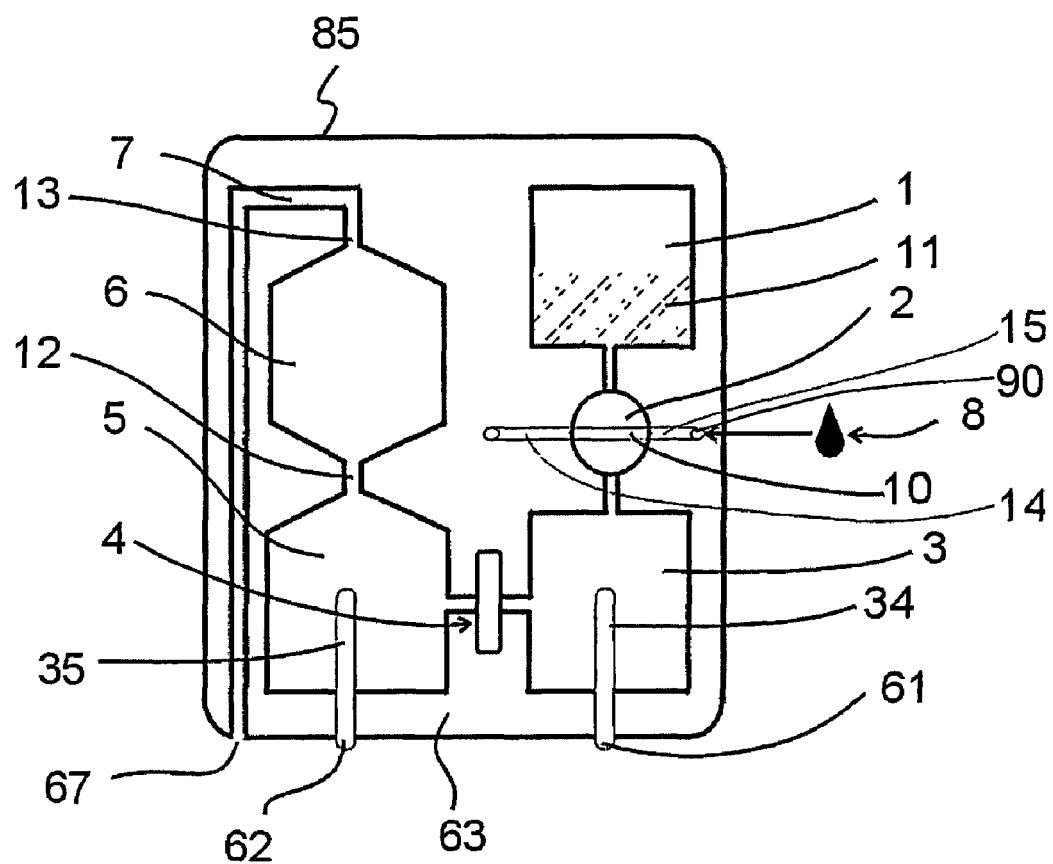

| | | |
|---|---|---|
| 3,122,431 A | 2/1964 | Coulter et al. |
| 3,395,343 A | 7/1968 | Morgan et al. |
| 3,549,994 A | 12/1970 | Rothermel et al. |
| 3,902,115 A | 8/1975 | Hogg et al. |
| 3,958,177 A | 5/1976 | Reeves et al. |
| 4,014,611 A | 3/1977 | Simpson et al. |
| 4,346,018 A | 8/1982 | Carter et al. |
| 4,485,175 A | 11/1984 | Ledis et al. |
| 4,521,729 A | 6/1985 | Kiesewetter et al. |
| 4,528,274 A | 7/1985 | Carter et al. |
| 4,600,880 A | 7/1986 | Doutre et al. |
| 4,607,526 A | 8/1986 | Bachenheimer et al. |
| 4,706,207 A | 11/1987 | Hennessy et al. |
| 4,738,827 A | 4/1988 | Pierotti |
| 4,745,071 A | 5/1988 | Lapicola et al. |
| 4,751,179 A | 6/1988 | Ledis et al. |
| 4,760,328 A | 7/1988 | Groves |
| 4,835,457 A | 5/1989 | Hanss et al. |
| 4,926,114 A | 5/1990 | Doutre |
| 4,962,038 A | 10/1990 | Carter et al. |
| 5,045,474 A | 9/1991 | Becker et al. |
| 5,077,017 A * | 12/1991 | Gorin et al. ............... 422/100 |
| 5,104,813 A * | 4/1992 | Besemer et al. ............ 436/179 |
| 5,198,749 A | 3/1993 | Guthrie et al. |
| 5,230,866 A * | 7/1993 | Shartle et al. ............... 436/179 |
| 5,231,005 A | 7/1993 | Russell et al. |
| 5,241,262 A | 8/1993 | Guthrie et al. |
| 5,257,984 A * | 11/1993 | Kelley ..................... 604/403 |
| 5,316,951 A | 5/1994 | Carver, Jr. et al. |
| 5,334,502 A | 8/1994 | Sangha |
| 5,348,859 A | 9/1994 | Brunhouse et al. |
| 5,393,496 A | 2/1995 | Seymour |
| 5,500,992 A | 3/1996 | Barnes et al. |
| 5,501,954 A | 3/1996 | Saldivar, Jr. et al. |
| 5,623,200 A | 4/1997 | Ogino |
| 5,716,852 A | 2/1998 | Yager et al. |
| 5,731,206 A | 3/1998 | Ledis et al. |
| 5,763,280 A | 6/1998 | Li et al. |
| 5,804,022 A | 9/1998 | Kaltenbach et al. |
| 5,834,315 A | 11/1998 | Riesgo et al. |
| 5,840,515 A | 11/1998 | Provost |
| 5,911,871 A | 6/1999 | Preiss et al. |
| 5,979,251 A | 11/1999 | James et al. |
| 6,046,019 A | 4/2000 | Goumeniouk |
| 6,111,398 A | 8/2000 | Graham |
| 6,230,896 B1 | 5/2001 | Lambert |
| 6,251,615 B1 | 6/2001 | Oberhardt |
| 6,319,209 B1 | 11/2001 | Kriz |
| 6,387,328 B1 | 5/2002 | Berndtsson |
| 6,663,833 B1 | 12/2003 | Stave et al. |

FOREIGN PATENT DOCUMENTS

| | | |
|---|---|---|
| EP | 0 549 414 A1 | 12/1992 |
| EP | 0 844 475 A2 | 11/1997 |
| EP | 1 182 457 A1 | 8/2000 |
| GB | 2 232 769 A | 12/1990 |
| GR | 1 002 424 | 8/1996 |
| JP | 5915849 A | 1/1984 |
| JP | 61205844 | 9/1986 |
| JP | 7301595 | 11/1995 |
| JP | 8015125 | 1/1996 |
| JP | 9304265 | 11/1997 |
| JP | 2002515601 | 5/2002 |
| WO | WO 93/01306 | 1/1993 |
| WO | WO 93 01306 A | 1/1993 |
| WO | WO 97/24600 | 7/1997 |
| WO | WO 98/54568 | 3/1998 |
| WO | WO 98/50777 | 11/1998 |
| WO | WO 99/01742 | 1/1999 |
| WO | WO 99/49319 | 9/1999 |
| WO | 9960379 | 11/1999 |
| WO | WO 00/07254 | 2/2000 |
| WO | WO 01/11338 A1 | 2/2001 |
| WO | WO 01/69292 A2 | 9/2001 |
| WO | WO 02/089670 A1 | 11/2002 |

OTHER PUBLICATIONS

Ed. M.M. Wintrobe et al., "Clinical Hematology", pp. 3-9, 1981, 8th ed., Lea & Febiger, Philadelphia, USA.

M. Madou, "Fundamenetals of Microfabrication", pp. 29-32, 66-70, 145, and 163-164, CRC Press LLC, 1997, ISBN 0-8493-9451-1.

Stevens, "Fundamentals of Clinical Hematology", pp. 6-7, and 301-304, W.B. Saunders Company, ISBN 0-7216-4177-6, Philadelphia, USA.

A.Y. Fu et al., "A Microfabricated fluorescene-activated cell sorter", Nature Biotechnology, vol. 17, Nov. 1999, pp. 1109-1111.

B.K. Gale et al., Micromachined Electrical Field-Flow Fractionation (u-EFFF) System:, Proceedings of the IEEE Annual International Workshop; pp. 119-124; Jan. 1997.

* cited by examiner (A)

(B)

(C)

US 7,771,658 B2

DISPOSABLE CARTRIDGE FOR CHARACTERIZING PARTICLES SUSPENDED IN A LIQUID

CROSS REFERENCE TO RELATED APPLICATIONS

This application claims priority under 35 U.S.C. 119 to Danish application PA 2003 00159 filed on Feb. 5, 2003, and under 35 U.S.C. 119(e)(1) to U.S. Provisional application Ser. No. 60/387,407 filed on Jun. 11, 2002, which are hereby incorporated by reference.

BACKGROUND OF THE INVENTION

1. Field of the Invention

The present invention relates to a disposable cartridge for characterizing particles suspended in a liquid, especially a self-contained disposable cartridge for single-use analysis, such as for single-use analysis of a small quantity of whole blood. The self-contained disposable cartridge facilitates a straightforward testing procedure, which can be performed by most people without any particular education. Furthermore, the apparatus used to perform the test on the cartridge, could be made simple, light and maintenance free, thus giving full portability and a large range of operation for the user. The invention provides steps for pre-analytic handling of samples such as hemolysing of red blood cells and inactivation of coagulation.

2. Description of the Background Art

Present instruments for particle characterization such as counting and sizing are fairly expensive, immobile and require operation by trained personnel. The consequence hereof has been that many instruments are placed in dedicated laboratories that are operated by specialized personnel. Furthermore, the samples to be analysed must be transported to this laboratory and the results are reported back to the requiree.

In WO 01/11338, which is hereby incorporated by reference, an apparatus is disclosed for characterizing particles suspended in a liquid, comprising a disposable cartridge and a docking station for removably receiving the cartridge. The cartridge comprises a housing with a first collection chamber bounded by a wall containing an orifice for the passage of the particles and having an inlet/outlet for connection to a source of positive or negative gas pressure, and components of a particle characterization device for characterizing particles passing through the orifice that are connectable from outside the housing. The docking station comprises a port for connection with a source of positive or negative gas pressure and forming a gas connection with the inlet/outlet when the cartridge is received in the docking station, and means for operative connection with the components of a particle characterization device when the cartridge is received in the docking station.

In WO 02/089670, which is hereby incorporated by reference, a device for sampling a small and precise volume of liquid is disclosed, comprising a movable member with a cavity for entrapment and displacement of an accurate part of a liquid sample.

It is a disadvantage of these prior art devices that several devices are used to perform an analysis, e.g. of a whole blood sample. The sample taking is performed with a separate device, and the sample has to be transferred to another device for sample preparation before it is finally transferred to a sensor for analysis.

In WO 99/01742 a disposable sampling device is disclosed for an apparatus for counting particles contained in a liquid. The sampling device is connectable in a defined position to the apparatus. The device has means for introducing a sample therein, means for metering a defined volume of the sample, means containing a defined volume of a diluting liquid, a diluting chamber, means for simultaneously directing the defined volume of sample and the defined volume of diluting liquid to the diluting chamber for obtaining therein a diluted sample, means for directing at least a portion of the diluted sample past particle counting means and signal transmitting means connecting the particle counting means and terminal means located at an outer boundary of the housing in a position corresponding to a location of terminal means of the apparatus when the housing is connected thereto in the defined position.

During blood analysis with the device described in WO 99/01742, the blood sample is pumped back and forth several times for dilution, mixing and analysis, and the flow system is closed so that the pressure in the system is increased and decreased above and below, respectively, atmospheric pressure during movement of the sample. Further, sample taking requires pumping with a membrane or another flow actuator causing entrance of blood into the flow system of the device. Thus, the above disclosed flow system is rather complicated.

The particle counting is, as described in WO 99/01742, performed in an open-ended tube so that the volume of diluted sample passing the particle counting sensor is very small.

The blood analysis, as described in WO 99/01742 does not take into account that particles of different kind and concentration might need pre-analytic separation, decomposition, staining or labeling in order to be accurately recorded by the sensing principle in account.

The blood test sequence as described in WO 99/01742 does not take into account that users without prior education herein should be able to learn how to perform this test themselves, i.e. no pre-analytical dilution steps should be required.

SUMMARY OF THE INVENTION

Thus, it is an object of the present invention to provide a cartridge for characterizing particles suspended in a liquid that enables sample taking, sample preparation, and particle characterization so that analysis may be performed within one device without a need for sample handling and sample transfer to another unit.

It is a further object of the present invention to provide a cartridge that is adapted for single-use to be discarded after analysis of one liquid sample.

It is another object of the present invention to provide a cartridge that has a simple flow system.

It is yet another object of the present invention to provide a flow system in the cartridge communicating with the surroundings so that the pressure in the flow system remains substantially constant at atmospheric pressure.

According to the present invention, the above-mentioned and other objects are fulfilled by a cartridge for characterizing particles suspended in a liquid, comprising a housing with a first mixing chamber and a first collection chamber separated by a wall containing an orifice for passage of the particles between the first mixing chamber and the first collection chamber. Particle characterization means are provided for characterizing particles passing through the orifice.

Sample taking may be performed through a bore in the outer surface of the housing for entrance of a liquid sample. The housing further comprises a sampling member that is movably positioned in the housing. The sampling member has a first cavity for receiving and holding a small and precise volume of liquid. In a first position of the sampling member, the first cavity is in communication with the bore for entrance of the liquid sample into the first cavity, and, in a second position of the sampling member, the first cavity is in communication with an inlet to the first mixing chamber.

Thus, the sampling member operates to receive and hold a precise volume of liquid sample and to transfer the sample to the inlet of the first mixing chamber.

Preferably, liquid to be sampled enters the cavities by capillary attraction causing a liquid flow. Utilization of capillary forces simplify the flow system, since no pumps, membranes, syringes or other flow generating means are, in contrast to WO 99/01742, needed to take the sample.

Thus, the bore may form a first capillary tunnel for entrance of a liquid sample by capillary attraction. The capillary tunnel is dimensioned so that, upon contact between the bore and liquid to be sampled, a sample of the liquid is drawn into the bore by capillary attraction.

Further, the first cavity may form a second capillary tunnel adapted for drawing the liquid sample into the first cavity by capillary attraction. Preferably, the first and second capillary tunnel has the same diameter, and it is also preferred that, in the first position, the first and second capillary tunnel extend along substantially the same longitudinal center axis.

Preferably, the sampling member is rotatable about an axis of rotation that is substantially perpendicular to a longitudinal axis of the first cavity.

Additionally or alternatively, the sampling member may be displaced in a direction substantially perpendicular to a longitudinal axis of the first cavity.

The surface of the first and second inner capillary tunnel walls may be hydrophilic whereby the capillary attraction of the liquid sample is facilitated. For example, the inner tunnel walls may be made of e.g. glass or polymers, such as polystyrene.

Alternatively, the capillary tunnel walls may be made of another type of material and covalently or non-covalently coated with a hydrophilic material, such as a polymer or a reagent.

The capillary tunnel may also include one or more reagents adhered or chemically bonded to the inner tunnel wall. These reagents serve the purposes of further facilitating the capillary attraction of the sample and optionally also causing a chemical reaction in the liquid sample, e.g. introducing anticoagulant activity in a blood sample. Such reagents may comprise heparin, salts of EDTA, etc.

Preferably, the sampling member is made of a polymer.

In accordance with a further aspect of the invention, an apparatus is provided for characterizing particles suspended in a liquid, comprising a cartridge as disclosed herein, and a docking station for removably receiving the cartridge, the docking station comprising connectors for operational connection with the particle characterization means when the cartridge is received in the docking station.

The cartridge may further comprise a cartridge port communicating with the first collection chamber for causing a liquid flow through the orifice, and the docking station may further comprise a corresponding port for forming a gas connection with the cartridge port when the cartridge is received in the docking station for application of a pressure causing a liquid flow through the orifice.

The particle characterization means may include a first electrode in the first mixing chamber and a second electrode in the first collection chamber, each electrode being electrically connected to a respective terminal member accessible at the outer surface of the cartridge for operational connection to the respective connector of the docking station when the cartridge is received in the docking station. Generally, it is preferred that all necessary electrical and fluid connections to the cartridge can be established by fitting the cartridge into the docking station, preferably by a simple push fit.

The first and second electrodes may facilitate particle characterization utilizing the well-known Coulter impedance principle, e.g. for counting and sizing of blood cells. This method has become a globally accepted method and is being used in the majority of haematology-analysers. Several thousand particles per second may be characterized with high precision and accuracy utilizing this principle.

With the electrical impedance technique it is possible to resolve the particle volume from the measurement. By maintaining a constant current across the orifice, the recorded voltage pulse from particles displacing the electrolyte in the orifice will have a height proportional to the volume of the particle. This is because particles can be considered non-conducting compared to the electrolyte, the electrical field (DC or RF) in the centre of the orifice is homogeneous, which is normally the case when the diameter D is smaller than the length l of the orifice (l/D>1), the particle d is to be considered small compared to the diameter of the orifice (d<0.2*D), only one particle passes through at a time and the particles are passed through the orifice along the length of the orifice.

Normally such apparatus is operated so that the flow through the orifice is into the first collection chamber.

Preferably, the length of the orifice is from 1 to 1000 μm, for example about 50 μm. Desirably the length of the orifice is chosen such that only one particle will be present in the orifice at the time when detecting particles of from 0.1 to 100 μm diameter. However, considerations to the homogeneity of the electrical field in the orifice may require a length of the orifice larger or equal to the diameter. The counts, of which some may be simultaneous counting of two particles, can be corrected mathematically by implementing a statistical estimation. The aspect ratio of the orifice, (length or depth divided by diameter) is preferably from 0.5:1 to 5:1, more preferably from 1:1 to 3:1.

Preferably, the largest cross-sectional dimension of the orifice is from 5 to 200 μm, for example 10 to 50 μm.

As explained above, the present invention provides in preferred aspects a sensor based on a membrane fabricated in e.g. a polymer sheet by laser ablation. The membrane has an orifice placed relatively in the centre of the membrane, which can be used for aspiration of particles suspended in a liquid, as the sensor is submerged into the liquid. This way of transporting particles into a measuring region is known for electrical characterization of particles by the Coulter principle (V. Kachel, "Electrical Resistance Pulse Sizing: Coulter Sizing", Flow Cytometry and Sorting, 2. ed., pp 80, 1990 Wiley-Liss, Inc.).

The cartridge may further comprise a breather inlet/outlet communicating with the surroundings for preservation of substantially ambient atmospheric pressure in the cartridge flow system for facilitation of liquid flow through the orifice.

Preferably, the cartridge is designed to be disposable after a single use. It is desirable that after use there is no need to clean the apparatus before it can be used in a new assay procedure with a new cartridge. Accordingly, escape of liquid from the cartridge at its entry into the docking station should be avoided. To this end the positioning of the orifice with respect to the breather inlet/outlet, the second chamber inlet/outlet and the particle characterization device components is preferably such that a volume of liquid sufficient for the desired particle characterization can be drawn or pumped through the orifice without the liquid passing out of the housing. Generally, it should be possible to pass a volume of liquid, which is at least 0.1 ml to 10 ml, e.g. 0.5 ml, through the orifice whilst particle characterization measurements are being made with no liquid leaving the cartridge.

The cartridge may comprise volume-metering means for determining the beginning and end of a period during which a predetermined volume of liquid has passed through the orifice.

Preferably, the volume metering means comprises a volume-metering chamber with an input communicating with the first collection chamber and an output, and wherein presence of liquid is detected at the input and at the output, respectively.

For example, presence of liquid may be detected optically due to changed optical properties of a channel configuration from being filled with air till when it is being filled with liquid. This could be constructed as reflectance or transmittance detection from the surface, where incident light is reflected from an empty channel and transmitted through a filled channel, thus giving a clear shift in the detected reflected or transmitted light.

It is preferred that the input and output of the metering chamber is formed by narrow channels for accommodation of only a small liquid volume compared to the volume of the metering chamber so that the actual positioning of the volume metering means, e.g. optical reflectance detection, in the channels do not substantially influence the accuracy of the volume metering means determination.

The first mixing chamber or the first collection chamber may constitute the volume metering chamber; however, it is preferred to provide an independent volume metering chamber facilitating positioning of the volume metering means, e.g. the optical reflectance detection.

The volume metering means may be positioned for sensing when liquid in the metering chamber is at or above respective levels in the volume-metering chamber.

The volume metering means may be used for sensing when the level of the liquid is such that the respective metering means are or are not filled with the liquid and may therefore serve for determining the beginning and end of a period during which a fixed volume of liquid has passed through the orifice. For example, particle characterization may begin when the level of the liquid just rises over the level of a first metering means and may end when the level of the liquid just rises over a second metering means, the volume of liquid passing through the orifice during this period being defined by the separation of the respective metering means.

Where the end point of the passage of a defined volume of liquid is the effective emptying of one chamber to below the level of the orifice, it is preferred that each of the collection and first mixing chambers (or at least that chamber from which liquid passes) has a transverse cross sectional area at the level of the orifice which is substantially less than the transverse cross sectional area of the chamber over a substantial part of the height of the chamber above the orifice.

According to a further aspect of the present invention a method is provided of operating a particle characterization apparatus comprising a cartridge as disclosed herein, the cartridge being demountable from the apparatus, the method comprising sampling liquid containing particles with the cartridge through the bore with the sampling member in its first position, positioning the cartridge in the apparatus, moving the sampling member to its second position, pumping liquid in the storage chamber through the first cavity and into the first mixing chamber together with the liquid sample, making particle characterizing measurements, disconnecting the cartridge from the apparatus, and discarding the cartridge.

Generally, in all embodiments it is preferred that all components, which are wet by the sample in use, are disposable and all non-disposable components can be re-used without cleaning.

It is an important advantage of the present invention that means for liquid sample preparation and analysis are integrated into a disposable cartridge. For example, the analytical steps comprise sampling of a precise amount of blood, dilution of the amount of blood and finally mixing the blood with diluent into a homogeneous solution. The analysis may include spectrophotometric analysis of the liquid.

Thus, according to the present invention, means are provided for unambiguously making a blood analysis, such as counting the blood cells in a small amount of blood coming from a droplet of capillary blood. Means are provided for taking an exact amount of blood sample, reagents present in the diluent may be added for e.g. dilution and/or chemical preparation of the sample, and the mixed sample and diluent flows through a sensor for analysis of individual blood cells and determination of the volume of the analysed quantum of liquid.

As a supplement a spectrophotometric measurement can be performed in order to quantify the content of e.g. haemoglobin.

The cartridge may comprise the following parts:
1. A liquid storage chamber
2. A blood-sampling device
3. A first mixing chamber
4. A flow through sensor arrangement
5. A first collection chamber
6. A volume metering arrangement comprised of a chamber and two connected flow channels
7. A hydraulic connection for moving the liquid through the cartridge The concept of the disposable unit can be further combined with the following additional parts:
A. Optical structures for optical liquid level measurement
B. Electrodes for liquid level measurement
C. Anti-coagulation treatment of surfaces
D. Reagents in the diluent for modification of e.g. blood cells
E. Mixing flee or baffle for assisted mixing
F. Multiple volume metering arrangements for altering volumes
G. A coating tape covering the sample inlet before use
H. A waste chamber for waste/overflow
I. A valve preventing liquid to exit through exhaust tube
J. An integrated piston or membrane to replace an external source of pressure
K. A window for spectrophotometric measurements The liquid storage chamber (part 1) holds the required amount of diluent used for the blood analysis. When the blood has been sampled into the cartridge, the diluent is flushed through the capillary to wash out the sampled blood and dilute it as required by the test. Dilutions of 100 to 100.000 times are considered to be normal ratings and dilutions of 500 to 10.000 times are preferred. The liquid storage chamber should preferably be constructed to facilitate total draining of the chamber. This would be accomplished by having a slanting of the bottom of the chamber.

The sampling unit (part 2) may comprise a capillary extending through a movable rod placed in a tight-fitting supporting body. The movable rod is used for entrapment of a precise amount of blood sample. When blood has filled the capillary by capillary forces, the rod is turned and/or displaced from its initial position in the supporting body, thus isolating the part of the capillary that extends through the rod.

After moving the rod in the supporting body into its second position the capillary forms a liquid path between the liquid storage chamber and the first mixing chamber (part 3). By applying a low pressure to the first mixing chamber the diluent and blood sample is forced into the first mixing chamber, where mixing will be performed by convection or subsequently by blowing bubbles into the mixing chamber.

The flow through sensor arrangement (part 4) is comprised of a small orifice in a membrane that establishes a liquid path from the first mixing chamber to the first collection chamber. On each side of the membrane (in the first mixing chamber and in the first collection chamber) an electrode is placed contacting the liquid.

The first collection chamber (part 5) forms a liquid priming function of the backside of the sensor system.

The volume metering system (part 6) is necessary for determination of the cell concentration. It comprises volume-metering chamber of a known volume with two relatively thin channels connecting the inlet at the bottom and the outlet at the top. Sensing of the liquid at the inlet and outlet can be applied by optical or electrical means.

The outlet of the volume metering system is connected through a channel (part 7) to a source of pressure for moving the liquid through the cartridge.

The additional parts to the concept are further described here:

Addition A: Optical detection by change of optical properties of a channel such as changed reflectance or transmittance due to replacement of air with liquid in the channel. The surface over the inlet and outlet of the volume-metering cell should be structured to optimize the coupling of the light into the channel. The presence of liquid in a transparent polymer channel will result in a transmission of the signals as opposed to a reflection when no liquid is present, which can be registered by optical sensors.

Addition B: Two electrodes for liquid level measurement are connected through the body of the cartridge into the inlet and outlet of the volume-metering cell respectively. The electrodes will be short-circuited through the saline liquid to the electrode placed in the first collection chamber, which can be registered through an external electrical arrangement.

Addition C: The anti-coagulation treatment of surfaces in the sampling structure can be achieved by having selected compounds adhered or chemically bonded to these surfaces. Examples of such compounds are heparin and salts of EDTA.

Addition D: Reagent in the diluent for modification of e.g. blood cells. This reagent can consist of one or several compounds capable of hemolysing the erythrocytes. In addition other compounds may be added in order to: stabilize leukocytes and/or thrombocytes, adjust the pH-value and osmotic pressure, minimize bacterial growth, modify the haemoglobin present and minimize batch to batch variations. The following examples have been included to provide information on relevant subjects related to the performance of a self-contained test cartridge.

Examples of compounds capable of selectively hemolysing the red blood cells are: mixtures of quaternary ammonium salts as described in e.g. U.S. Pat. Nos. 4,485,175; 4,346,018; 4,745,071; 4,528,274; and 5,834,315.

Examples of compounds capable of, during the hemolysis of the red blood cells, stabilizing the leukocytes are N-(1-acetamido)iminodiacetic acid, procaine hydrochloride as described in e.g. U.S. Pat. No. 4,485,175 and 1,3-dimethylurea as described in e.g. U.S. Pat. No. 4,745,071. In addition N-(1-acetamido)iminodiacetc acid is proposed to further assist the quaternary ammonium salts in minimizing debris stemming from hemolysed red blood cells as described in e.g. U.S. Pat. No. 4,962,038 and adjust the pH-value (see below).

Examples of compounds added in order to adjust the pH-value and not least importantly the osmotic pressure of the diluent are: N-(1-acetamido)iminodiacetic acid, sodium chloride, sodium sulphate as described in e.g. U.S. Pat. No. 4,485,175 and U.S. Pat. No. 4,962,038.

Examples of compounds capable of minimizing bacterial growth are: 1,3-dimethylolurea and chlorhexidine diacetate as described in e.g. U.S. Pat. No. 4,962,038.

Examples of compounds added to convert the hemoglobin species to an end-product suitable for spectrophotometric analysis are: potassium cyanide as described in e.g. U.S. Pat. Nos. 4,485,175; 4,745,071; 4,528,274 and tetrazole or triazole as described in WO 99/49319.

Examples of particles or compounds which may be added in order to introduce a tool for minimizing variation between different batches of the disposable device are: latex beads of known size and glass beads of known size.

Addition E: If assisted mixing is required the first mixing chamber might optionally include a mixing flee or a baffle. A magnetic flee may be used to force the convection through an externally moving magnetic field. A baffle may be used to mechanically stir the liquid when moved by an externally connecting mechanical device. This could be required if mixing with bubbles, such as bubbles blown into the sample through the sensor, is not adequate or possible.

Addition F: Multiple volume metering arrangements can be successively included if the test must deal with different concentrations of the different particles.

Addition G: A lid or coating tape may be used to cover the sample inlet before use. This ensures a clean sampling area at the origination of the test.

Addition H: A waste chamber may be applied at the outlet of the volume-metering cell for waste or overflow of liquid.

Addition I: At any connection ports, e.g. the connection port to the pressure source, a small valve can be integrated to prevent liquid to leak out of the cartridge.

Addition J: A piston or membrane can be integrated into the cartridge to include a source of pressure for moving the liquid. The piston or membrane could be moved by a mechanical force provided by the instrument.

Addition K: An optical window can be integrated into the cartridge in order to perform optical measurements such as spectrophotometric detection of the haemoglobin content in a blood sample.

The methods described can be combined to give the best solution for the final application. The disposable sensor is particularly usable where portable, cheap, simple or flexible equipment is needed, such as in small laboratories, in measurements in the field or as a "point of care" ("near-patient") diagnostic tool.

When using the Coulter principle the diluent for use in the apparatus according to the invention may contain inorganic salts rendering the liquid a high electrical conductivity. When sample is applied to the electrolyte, the electrolyte to sample volumes should preferably be higher than 10. Sample preparation should preferably result in between 1.000 to 10.000.000 particles per ml and more preferably between 10.000 and 100.000 particles per ml. A mixing of the sample after adding electrolyte is recommended. Particle diameters should preferably be within 1 to 60 percent of the orifice diameter and more preferably between 5 to 25 percent of the orifice diameter. Volume flow should preferably be from 10 µl to 10 ml per minute and more preferably between 100 µl and 1 ml per minute. For the measurement a constant electrical current of approximately 1 to 5 mA should preferably be applied. The source of electrical current should preferably have a signal to noise ratio (S/N) better than 1.000. The response from the electrodes can be filtered electronically by a band-pass filter.

According to yet another aspect of the invention a cartridge is provided comprising a housing with a first mixing chamber and a first collection chamber separated by a wall containing a first orifice for the passage of the particles between the first mixing chamber and the first collection chamber, first particle characterization means for characterizing particles passing through the first orifice, a bore in the outer surface of the housing for entrance of the liquid sample, communicating with a first sampling member positioned in the housing for sampling the liquid sample and having a first cavity for receiving and holding the liquid sample, the member being movably positioned in relation to the housing in such a way that, in a first position, the first cavity is in communication with the bore for entrance of the liquid sample into the first cavity, and, in a second position, the first cavity is in communication with the first mixing chamber for discharge of the liquid sample into the first mixing chamber.

The cartridge may further comprise a second mixing chamber and a second collection chamber separated by a second wall containing a second orifice for the passage of the particles between the second mixing chamber and the second collection chamber, second particle characterization means for characterizing particles passing through the second orifice.

In one embodiment of the invention, the first cavity is in communication with the first mixing chamber, when the first sampling member is in its first position, for entrance of liquid from the first mixing chamber into the first cavity, and, in a third position of the first sampling member, the first cavity is in communication with the second mixing chamber for discharge of the liquid in the first cavity into the second mixing chamber.

In another embodiment of the invention, the cartridge further comprises a second sampling member positioned in the housing for sampling a small and precise volume of liquid from the first mixing chamber and having a second cavity for receiving and holding the sampled liquid, the member being movably positioned in relation to the housing in such a way that, in a first position, the second cavity is in communication with the first mixing chamber for entrance of liquid from the first mixing chamber into the first cavity, and, in a second position, the second cavity is in communication with the second mixing chamber for discharge of the sampled liquid in the second cavity into the second mixing chamber.

The cartridge may further comprise a reagent chamber positioned adjacent to the first mixing chamber for holding a reagent to be entered into the first mixing chamber.

Preferably, the cartridge further comprises a breakable seal separating the reagent chamber from the first mixing chamber.

With this embodiment, different chemical treatment of different parts of the liquid sample may be performed.

Also with this embodiment, further dilution of the liquid sample may be performed.

Figure 2:
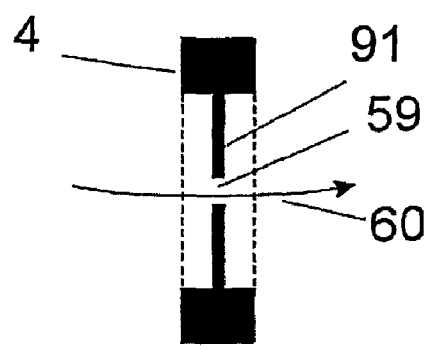
Figure 3:
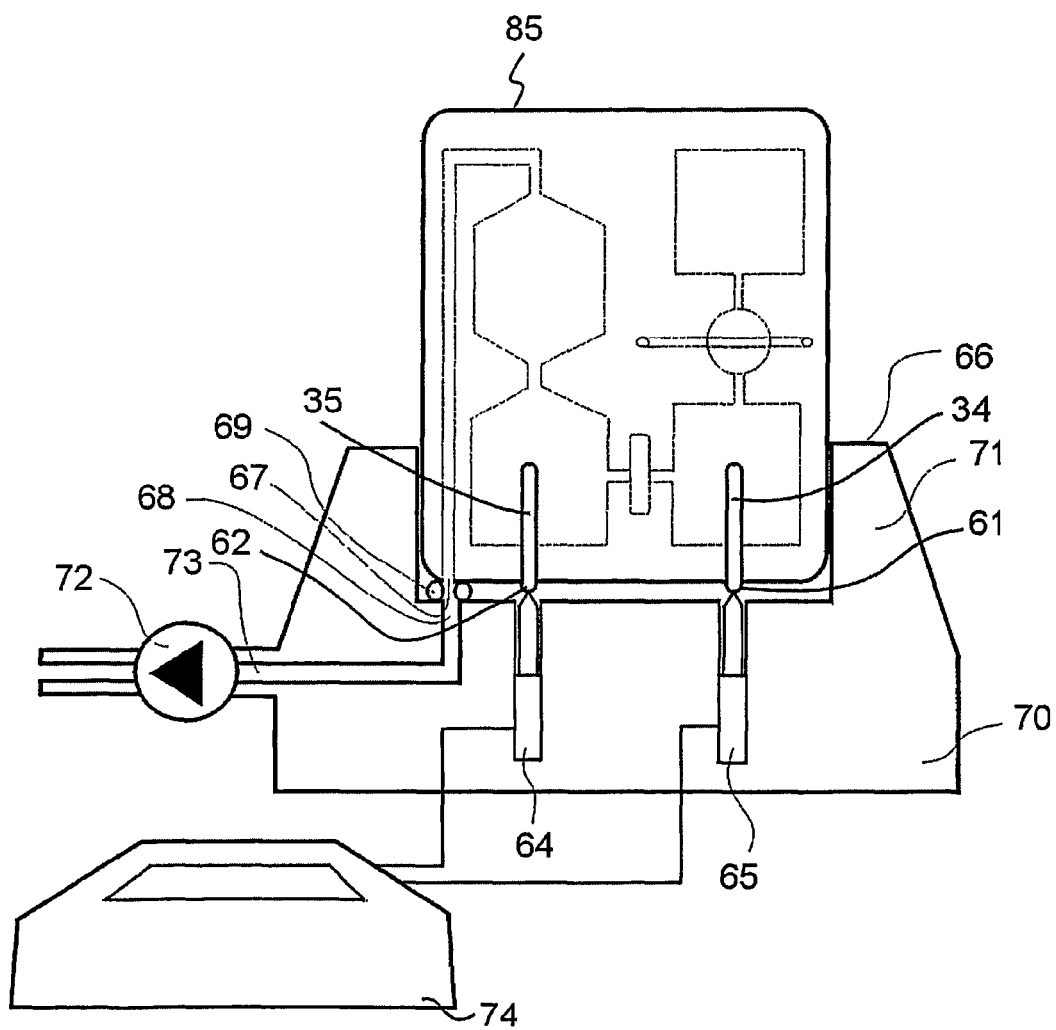
Figure 4:
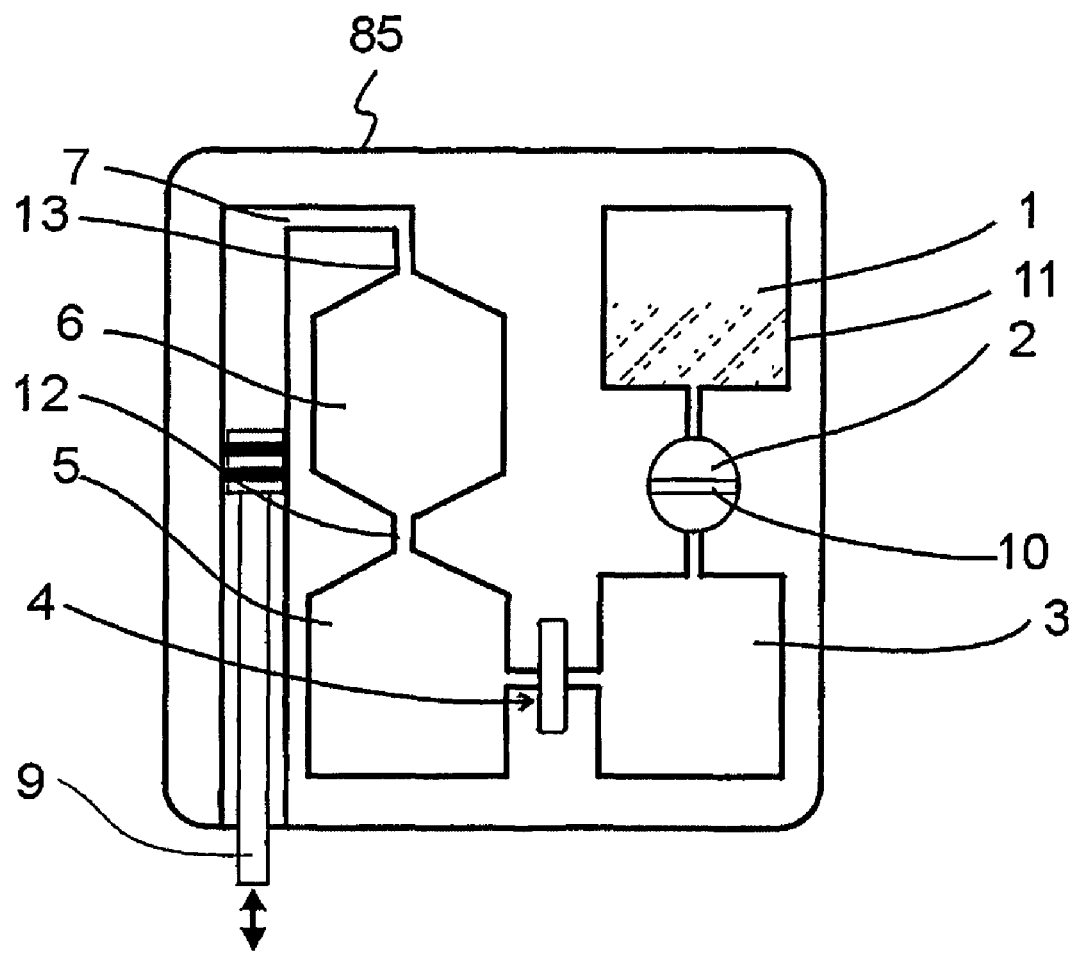
Figure 5:
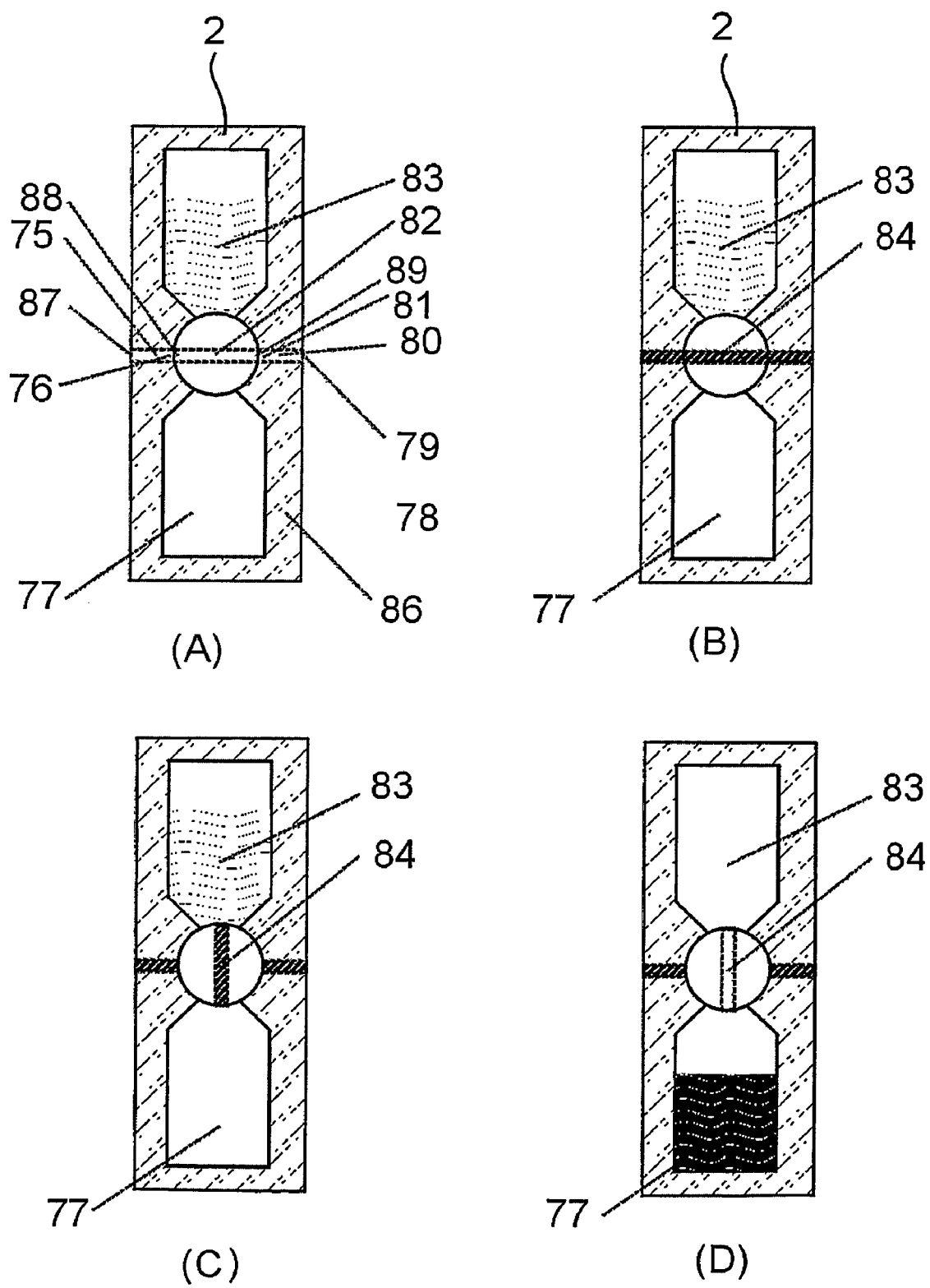
Figure 6:
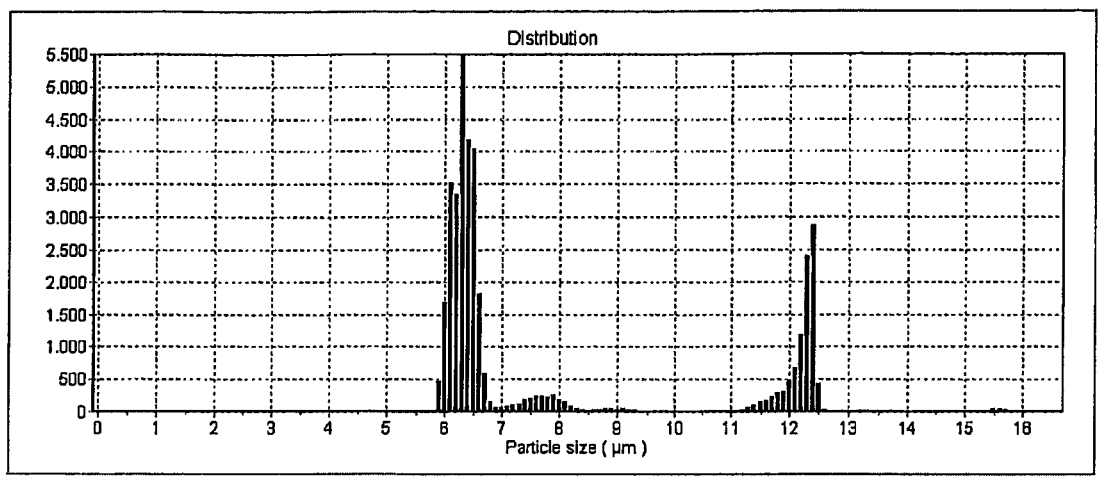
Figure 7:
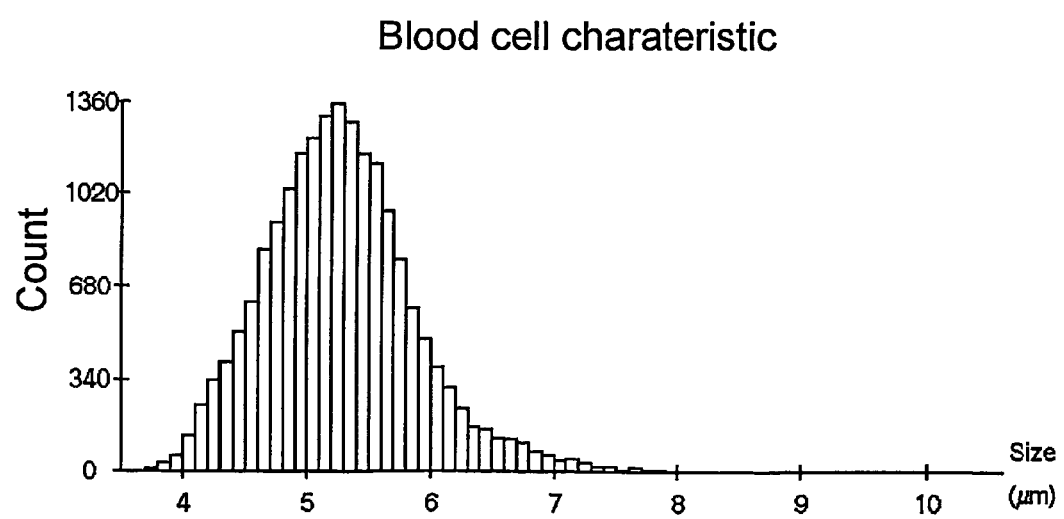
Figure 8:
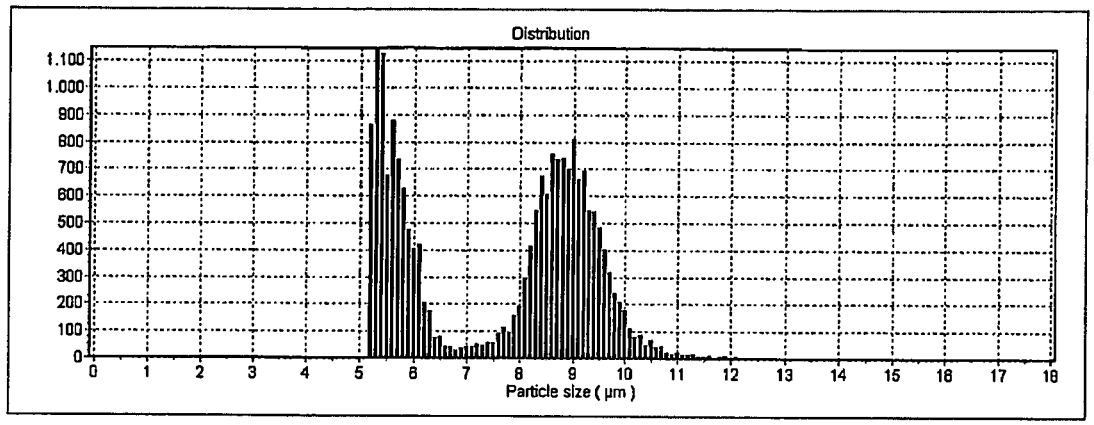
Figure 9:
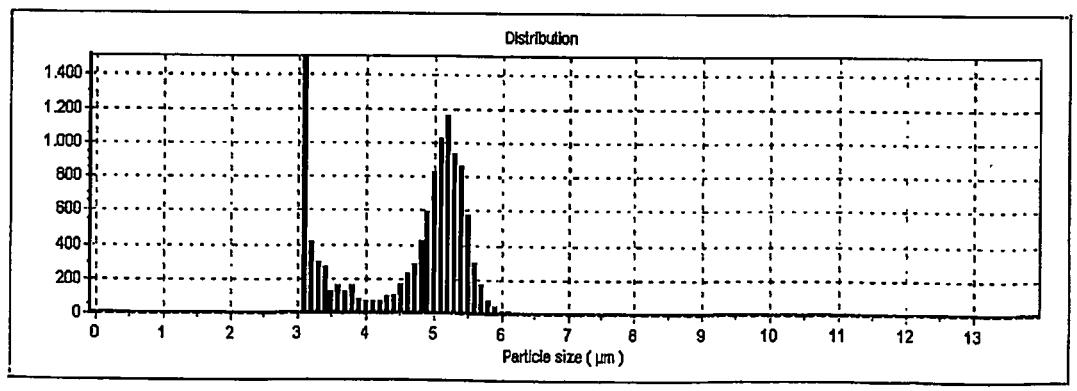
Figure 10:
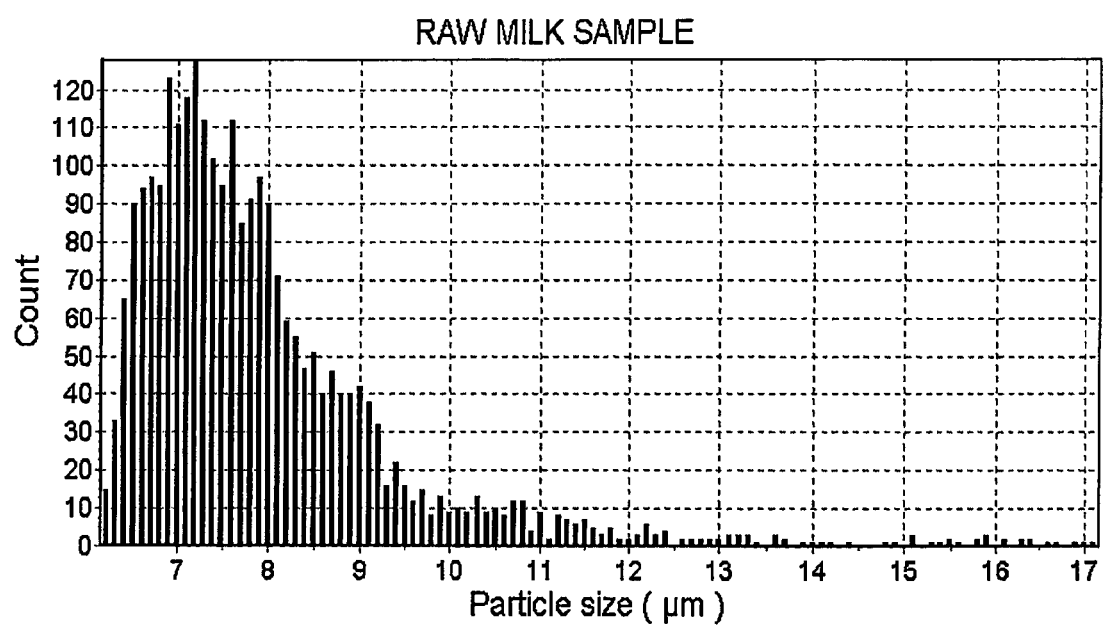
Figure 11:
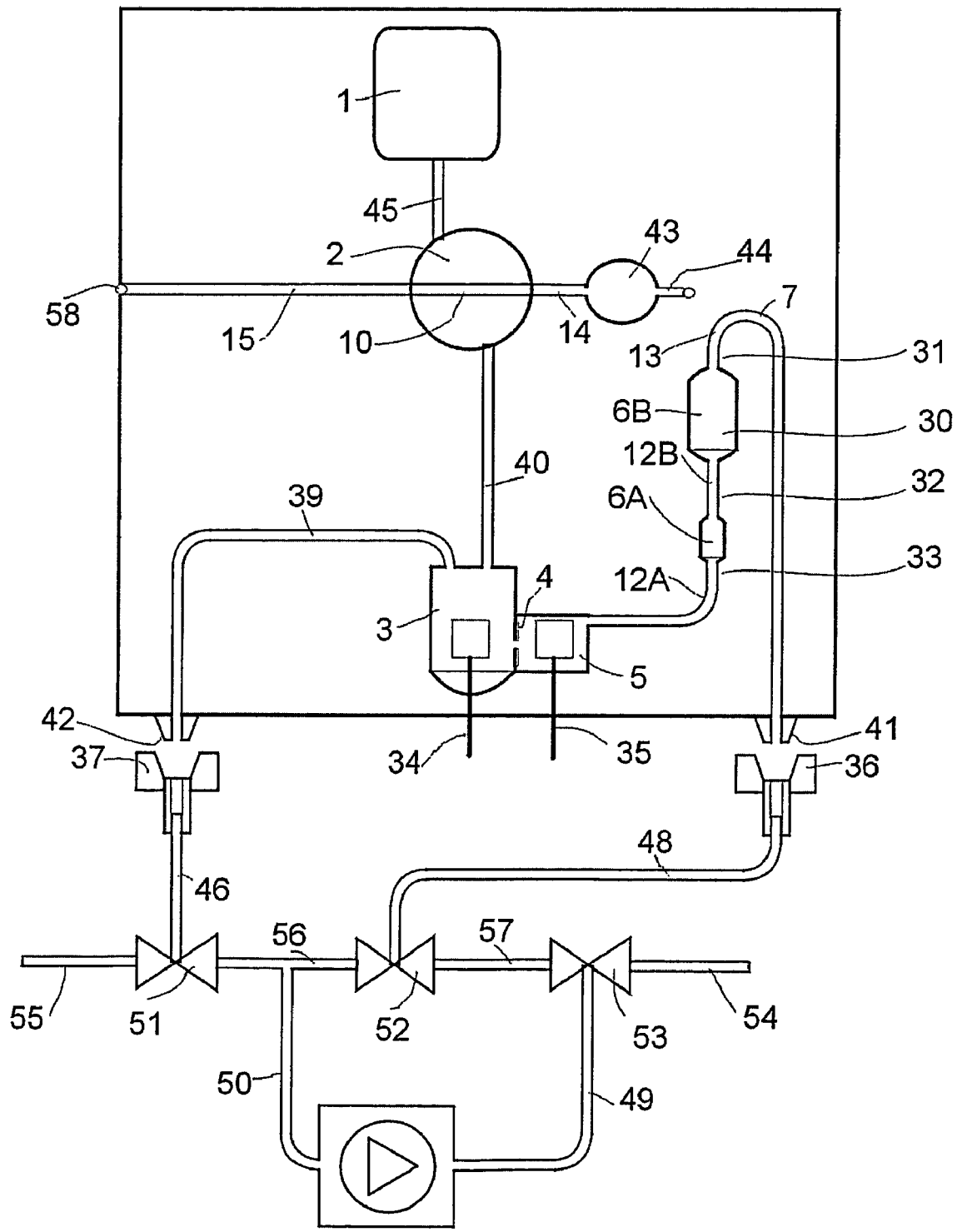
Figure 12:
Figure 12:
Figure 12:
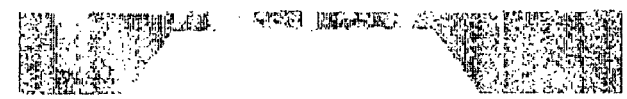
Figure 13:
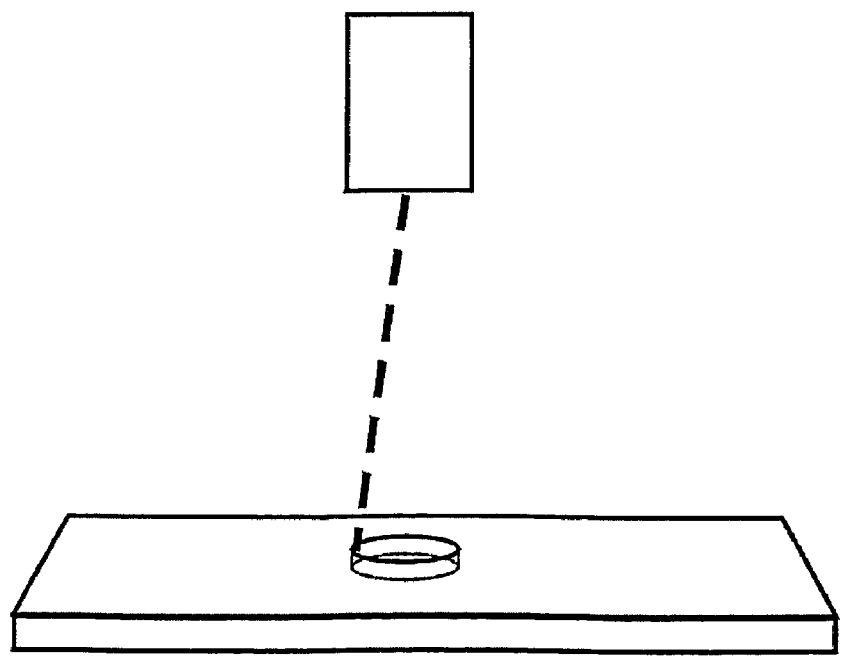
Figure 14:
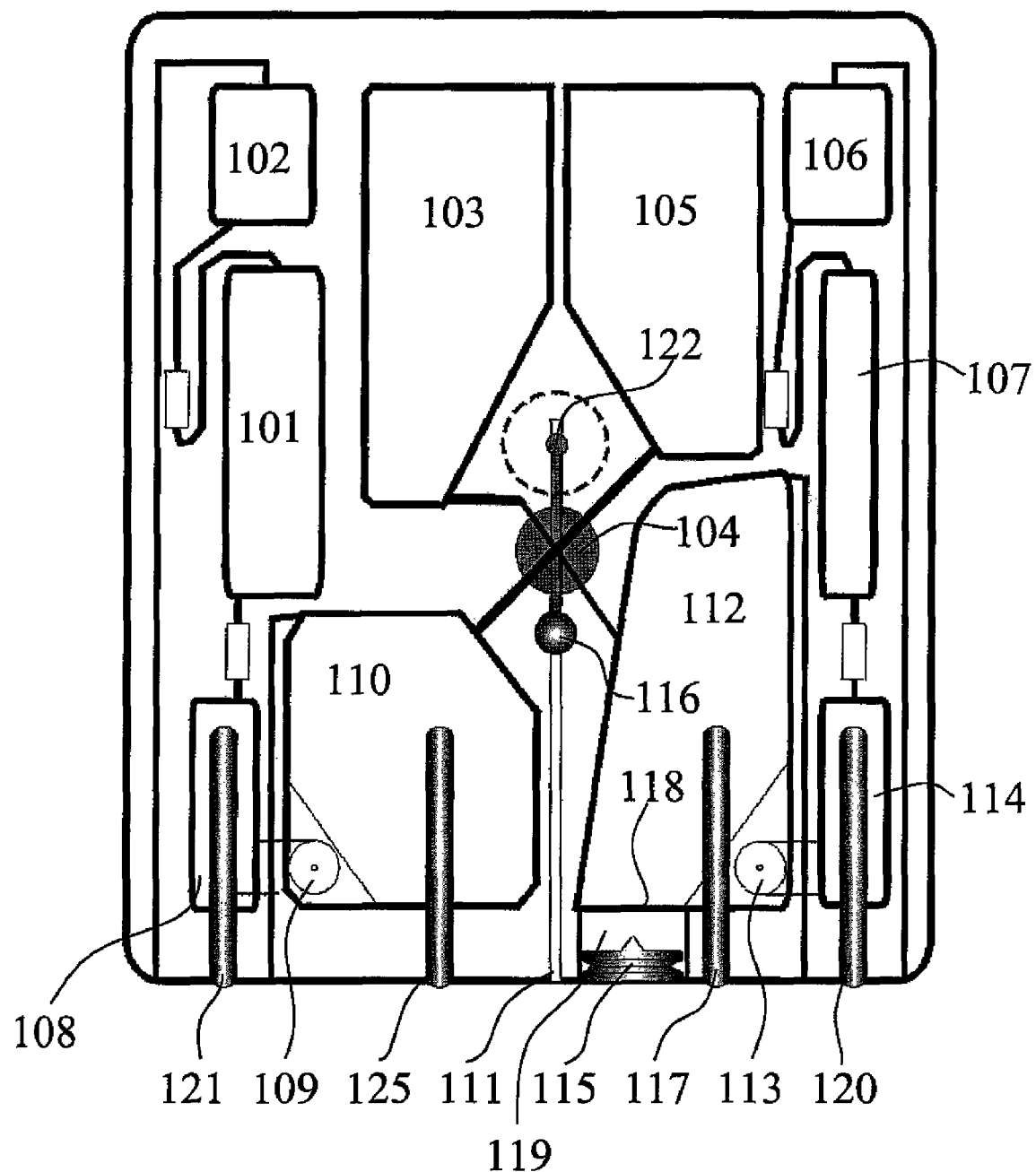
Figure 15:
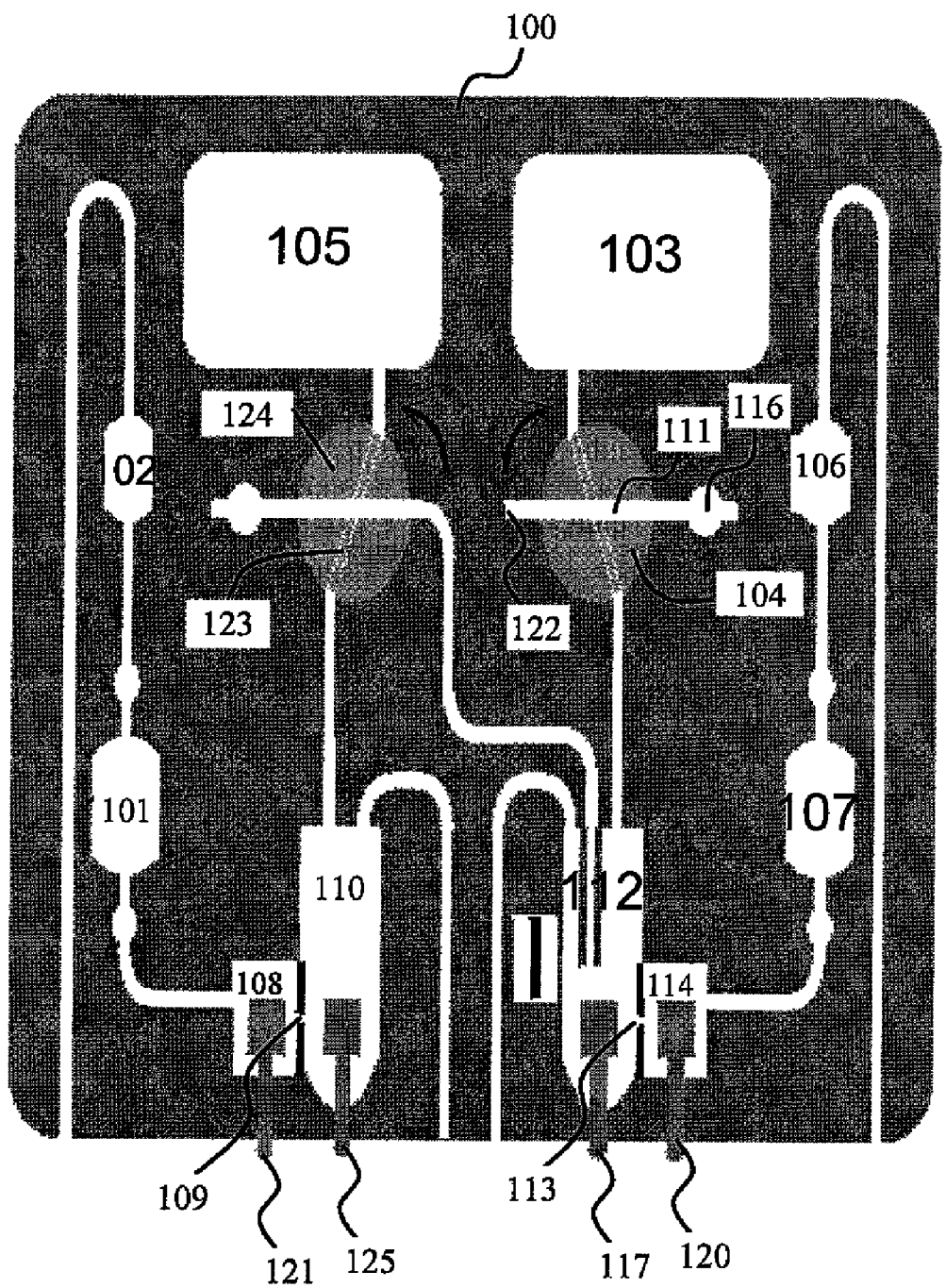
Figure 16:
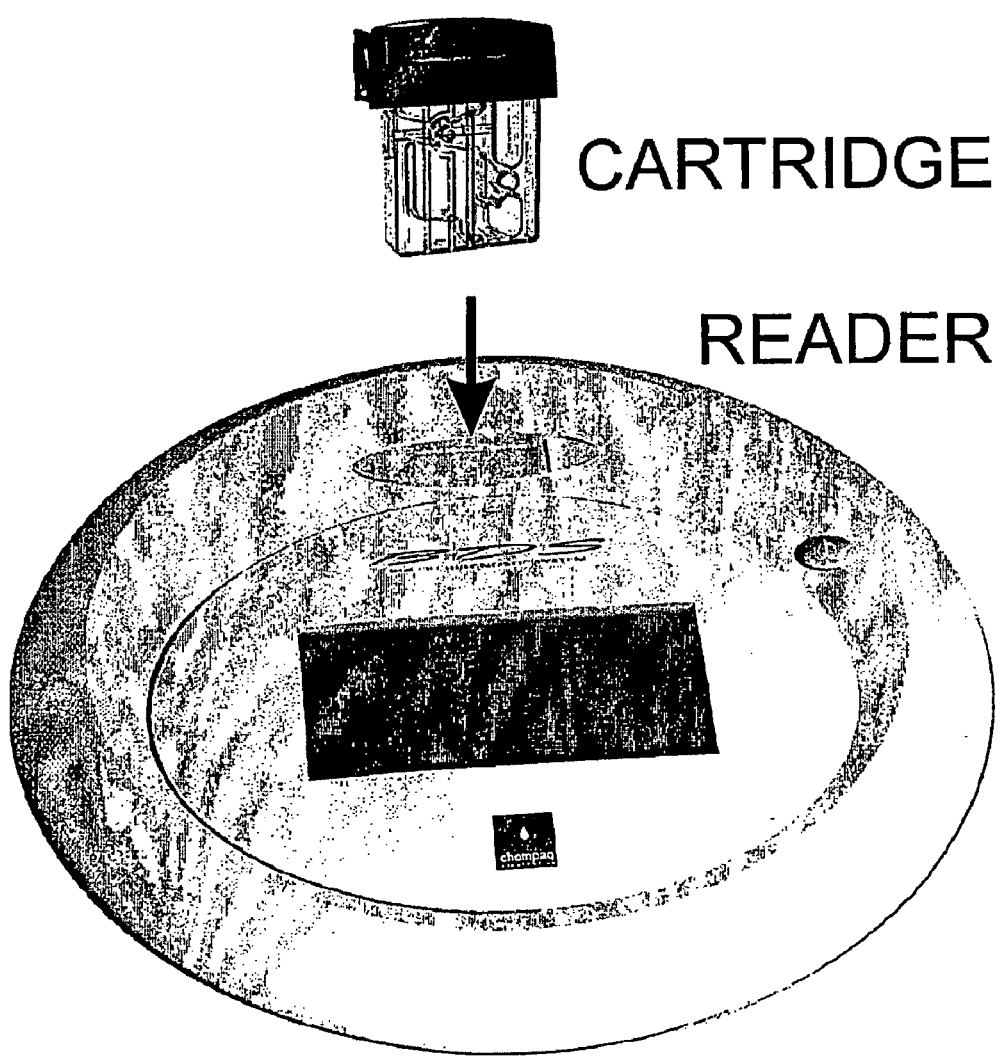

BRIEF DESCRIPTION OF THE DRAWINGS The invention will be further described and illustrated with reference to the accompanying drawings in which:

FIG. 1 shows a cross sectional side view through the components of a disposable unit 85, referred to as the cartridge, FIG. 2 shows the flow-through sensor concept FIG. 3 comprises an apparatus based on the disposable cartridge, a docking station 66 and a reader 74, FIG. 4 shows the cartridge with a build in piston, FIG. 5 schematically illustrates the sampling procedure, FIG. 6 is a plot of results obtained in Example 1, FIG. 7 is a plot of results obtained in Example 2, FIG. 8 is a plot of results obtained in Example 3, FIG. 9 is a plot of results obtained in Example 4, FIG. 10 is a plot of results obtained in Example 5, FIG. 11 is a schematic illustration of the cartridge and hydraulic connections in example 6, FIG. 12 is a plot of the process described in example 7, FIG. 13 is a plot of the process described in example 8, FIG. 14 shows schematically a second embodiment of the cartridge, FIG. 15 shows schematically a third embodiment of the cartridge, and FIG. 16 shows in perspective an apparatus according to the invention.

DETAILED DESCRIPTION OF THE PREFERRED EMBODIMENTS

FIG. 1

A disposable cartridge with a housing 85 for blood analysis comprises a liquid storage chamber 1 containing a liquid diluent 11, a first sampling member 2 positioned in the housing 85 for sampling a blood sample 8 and having a cavity 10 for receiving and holding the blood sample 8, the member 2 being movably positioned in relation to the housing 85 in such a way that, in a first position, the cavity 10 is in communication with a bore 90 for entrance of the blood sample 8 into the cavity 10 by capillary forces, and, in a second position, the cavity 10 is in communication with the liquid storage chamber 1 and a mixing chamber 3 for discharge of the blood sample 8 diluted by the liquid diluent 11 into the mixing chamber 3. The mixing chamber 3 is separated by a wall containing an orifice 59 from and a collection chamber 5 for the passage of the blood sample 8 between the mixing chamber 3 and the collection chamber 5. The wall containing the orifice 59 constitutes a part of a flow-through sensor 4.

A volume metering arrangement is connected to the collection chamber comprising a volume metering chamber 6 having the size of the volume to be measured during the measurement with two connecting channels 12, 13 of relatively diminutive internal volumes for registering liquid entry and exit by optical or electrical means, from the volume metering chamber a channel 7 leads out to a connection port 67 where a pressure can be applied.

FIG. 2

The flow-through sensor 4 has a dividing wall 91 with a relatively narrow orifice 59 for the passage of particles suspended in liquid. The orifice serves as a sensing zone for detection and measurement of the individual cells. The orifice in the sensor may be formed as a count orifice for counting and sizing particles by an impedance method known as Coulter counting. Particles can be aspirated through the orifice by pressure driven flow in either direction. When a saline or other electrolytic liquid solution is added to the chambers, the two chambers will be electrically isolated from each other except for the route for current flow provided by the passage through the orifice.

FIG. 3

The chambers on each side of the flow through sensor may have electrodes 34, 35 extending from an external terminal 61, 62 through the base wall 63 of the disposable unit and into a configuration facing the inside of its respective chamber. The cartridge is placed in a docking station 66 in a portable apparatus in order to carry out the test. The docking station 66 has a cup shaped housing having a base 70 and a circumambient sidewall 71. In the base 70 there are respective spring loaded electrical connectors 64, 65 for contacting the terminals 61, 62 of the cartridge automatically when the cartridge is received as a push fit into the docking station. There is also a conduit 68 passing through the base wall 70 aligned with the conduit 67 of the cartridge. Conduit 67 at its opening into the upper face of the wall 70 has a seal 69, such as e.g. an O-ring for forming a gas tight connection with the lower face of the base wall 63 of the cartridge. A vacuum pump 72 is connected by a line 73 to the lower end of the conduit 68. In a modification of the apparatus, the vacuum pump 72 can be reversed so as to apply positive gas pressure to the conduit 68. Schematically indicated at 74 are the further conventional components of a Coulter counter including all the electronic circuitry and display equipment needed for the operation of the apparatus. A general perspective view of the cartridge and reader is shown in FIG. 16.

FIG. 4

As an alternative to the gas pump a piston 9 could be build into the cartridge for directly appliance of a negative or positive pressure.

FIG. 5

FIG. 5 schematically illustrates the blood sampling operation. The illustrated part of the cartridge 2 includes the liquid storage chamber 83 for storing a diluent for diluting the sample and the first mixing chamber 77 for mixing the sample 84 and the diluent. This figure schematically illustrates a device for sampling a small and accurate volume of liquid in accordance with the present invention. The device 10 comprises a first member 86 with a first opening 87 for entrance of a liquid sample into a bore 75 in the first member 86 and with a second opening 76 for outputting the liquid sample from the bore 75. The bore 75 forms a capillary tunnel. The first opening 87 of the first member 86 may be brought into contact with a liquid 8 (shown in FIG. 1), 84 to be sampled so that the liquid 84 may flow through the first opening 87 into the bore 75 and out of the second opening 76 by capillary attraction. The device 12 further comprises a sampling member 78 with a first cavity 82 for receiving and holding the liquid sample 84 and having a third opening 88 communicating with the first cavity 82. The first cavity forms a capillary tunnel with essentially the same diameter as the bore 75. The sampling member 78 is a circular cylinder that is movably positioned in relation to the first member 86. During sampling of the liquid, the sampling member 78 is positioned in the illustrated first position in relation to the first member 86 wherein the second opening 76 is in communication with the third opening 88 so that sampled liquid may flow through the second 76 and third opening 88 into the first cavity 82 by capillary attraction. The third opening 88 may be disconnected from the second opening 76 in a second position of the sampling member 78 in relation to the first member 86 so that the liquid sample 84 contained in the first cavity 82 is disconnected from the bore 75.

The sampling member 78 is inserted into a third cavity of the first member 86 for receiving and accommodating a part of the sampling member 78. The sampling member 78 may be displaced between the first and second position along a longitudinal axis of the sampling member 78 that is also substantially perpendicular to a longitudinal axis of the first cavity 82. The sampling member 78 may also be rotatable about a longitudinal axis that is substantially perpendicular to a longitudinal axis of the first cavity 82. In the first position, the first 75 and second 82 capillary tunnels extend along substantially the same longitudinal center axis.

In the illustrated embodiment the first member 86 is symmetrical and has a fourth cavity 80 with openings 81, 79 opposite the bore 75, and the sampling member 78 has an opening 89 opposite the opening 88 so that, in the first position, a capillary tunnel extends through the first 86 and the second 78 member and communicates with the environment through openings 87, 79. Thus, air may escape from the capillary tunnel through opening 79. Further, in the first position, a part of the liquid entering the first cavity 82 will leave the cavity 82 through opening 89 thereby ensuring that the cavity 82 has been completely filled with liquid during liquid sampling eliminating the risk of sampling with a reduced sample volume leading to low accuracy sampling.

FIG. 5a illustrates the device 2 ready for receiving the liquid. In FIG. 5b, a sample has entered into the capillary tunnel 82, and in FIG. 5c the sampling member 78 has been rotated into the second position for isolation of an accurate volume of the sample 84, and finally FIG. 5d illustrates that the sample 84 has been washed out of the capillary tunnel 82 and into the first mixing chamber 77 by the diluent.

Example

The capillary tunnel forming the first cavity 82 may have a length of 8 mm and a diameter of 0.9 mm for containing a liquid sample of 5.089 µL.

Example

The capillary tunnel forming the first cavity 82 may have a length of 5 mm and a diameter of 0.5 mm for containing a liquid sample of 0.982 µL.

Example

The capillary tunnel forming the first cavity 82 may have a length of 3 mm and a diameter of 0.3 mm for containing a liquid sample of 0.212 µL.

FIG. 6

Example 1

Sizing of Polymer Beads

A mixture of 5 µm and 10 µm particles suspended in electrolyte was aspirated through the orifice of the apparatus shown in FIG. 3. The numbers of particles detected and the size of each detected particle were recorded. A bimodal distribution of detected particle size is clearly seen in FIG. 6.

FIG. 7

Example 2

Red Blood Cell Counting

Measurement of blood cells has been performed and the result is shown in FIG. 7. Red blood cells are normally around 5 to 7 µm in diameter and are the most frequent in whole blood, as can be seen on the FIG. 7. The distribution is a Gaussian curve, as it should be expected. Blood counts can be used in clinical diagnostics. It is fairly simple to count erythrocytes, leukocytes and thrombocytes by impedance measurements, which are considered the basic parameters for haematology (see "Fundamentals of Clinical Haematology", Stevens, W.B. Saunders Company, ISBN 0-7216-4177-6).

FIG. 8

Example 3

White Cell Counting using a Diluent Containing a Reagent-Composition Selected so as to Preserve all Blood Cells Material Cartridge and apparatus containing the functions as described in the present invention, Isoton, Beckman Coulter (prod. no. 24655) containing: sodium chloride 7.9 g/L, potassium chloride 0.4 g/L, disodiumhydrogenphosphate 1.9 g/l, sodiumdihydrogenphosphate 0.2 g/L, disodium-EDTA 0.4 g/L and sodium fluoride 0.3 g/L.

Vacutainer, K3E, Becton & Dickinson, prod. No. 367652.

Bayer, ADVIA-120 equipment.

Performance

The full sequence of the procedure was as follows:

Collection of a venous blood sample in a vacutainer tube.

Leaving the sample, for the sedimentation process to proceed, for three hours.

Extraction the plasma phase with the major part of the buffy-coat section included Performing analysis using the Bayer Advia 120 equipment for obtaining a comparative value for the content of leukocytes.

Adding 5.00 ml isoton solution as diluent to the chamber of the test rig

Adding 10.0 µl of sample to the chamber

Mixing liquids in the chamber

Starting test sequence on the computer (starts the pump and readies the sampling)

When the liquid reaches the first level electrode sampling is started

When the liquid reaches the second level electrode the sampling is stopped

Sampled values are saved in a file

The file is opened with a "pulse-viewer" for data analyzing and calculation of the result using a method of calculation involving subtraction of, with the leukocytes overlapping red blood cells.

Results

Bayer Advia-120: 11.96×10^9 leukocytes/L

Test-rig: 11.92×10^9 leukocytes/L

Difference in accuracy: (11.96−11.92)/11.96=0.33%

FIG. 9

Example 4

White Cell Isolation using a Diluent Containing a Reagent Composition Selected so as to Primarily Hemolyse the Red Blood Cells Material Cartridge and apparatus containing the functions as described in the present invention, Diluent containing: procaine hydrochloride 0.10 g/L, 1,3-dimethylolurea 0.90 g/L, N-(1-acetamido)iminodiacetic acid 1.28 g/L, dodecyltrimethyl ammonium chloride 7.51 g/L and sodium chloride 0.03 g/L.

Vacutainer, K3EDTA, Becton & Dickinson, prod. No. 367652.

Performance

The full sequence of the procedure was as follows:

Collection of a venous blood sample in a vacutainer tube.

Leaving the sample, for the sedimentation process to proceed, for three hours.

Extraction the plasma phase with the major part of the buffy-coat section included Adding 2.000 ml diluent as described above to the chamber of the test rig Adding 4.0 µl of sample to the chamber Mixing liquids in the chamber Starting test sequence on the computer (starts the pump and readies the sampling)

When the liquid reaches the first level electrode sampling is started

When the liquid reaches the second level electrode the sampling is stopped

Sampled values are saved in a file

The file is opened with a "pulse-viewer" for data analyzing and generation of the result.

Results

As can be seen in the histogram in FIG. 6 the particle population corresponding to the leukocytes is easily identified in the absence of the red blood cells.

FIG. 10

Example 5

Counting Somatic Cells

Milk quality is essential for farmers, diary producers and consumers. Farmer has to deliver milk of a certain quality, which is controlled by the so-called Somatic Cell Count (SCC). In milk quality tests somatic cells in the milk are counted to determine infections (clinical mastitis). A limit of 400.000 cells pr. ml. has to be met by the farmers for dairy resale. Change of diet, stress or mastitis lead to higher SCC levels, thus lowering the quality of the milk and consequently lowering the price per unit volume. A cheap cell counter will help farmers and diary producers monitor SCC-level.

FIG. 11

Example 6

A Blood Diagnostic System

This is an example of a 3 part differential white blood cell count (monocytes, lymphocytes, granulocytes), thrombocytes count and haemoglobin measurement and the corresponding instrumentation and cartridge realized through the present invention.

A three-part differentiation of white blood cells, thrombocyte counter with measurement of haemoglobin can be achieved with the specified components.

A reagent for selectively lysing red blood cells is added to the diluent in the storage chamber 1. When the whole blood 8 is added to the opening 58 of the first capillary section 15, the blood will be dragged in to the capillary and through the middle section 10 and last section 14 of the capillary. The last section of the capillary is connected to a fill-chamber 43 for visually verification of the filling. The fill-chamber 43 is connected through a conduct 44 to open air.

The blood filled middle section of the capillary is part of a knob 2 that can be moved to a second position, connecting the ends of the capillary to two other conducts, a conduct 45 connected to the storage chamber 1 and a second conduct 40 connected to the first mixing chamber 3 respectively. A third conduct 39 is leading from the first mixing chamber to a port opening 42 in the cartridge. The port opening is connected through a counter port opening 37 in the apparatus, through a tubing 46 to a three-position valve 51 and directed through the two positions of the valve to open air through a second tubing 55 or through a third tubing 50 to the suction port of a membrane pump 47.

When the blood and diluent with reagent has been sucked into the first mixing chamber, the blood can be mixed by blowing bubbles through the orifice of the sensor 4. The air pressure is applied through the collection chamber 5, via a fourth conduct 12A, a small volume chamber 6A, a fifth conduct 12B, a large volume chamber 6B and a sixth conduct 7 directed to an opening port 41 in the cartridge. A counter port 36 in the apparatus is connected through a fourth tubing 48 to a second three position valve 52, which has positions to direct to both vacuum through a fifth tubing 56 to the suction port of the membrane pump, or to the exhaust of the membrane pump, through a third two position valve 53 and a sixth tubing 49, the third valve having two positions for the connection and for directing the pump exhaust to open air through a seventh tubing 54 respectively.

After mixing the diluted and lysed blood (red blood cells is removed) it is ready to be measured. The first mixing chamber is connected through the first valve to open air and the collection chamber is connected through the second valve to the suction port of the pump. The exhaust of the membrane pump is connected through the third valve to open air. As the blood and diluent flows from the first mixing chamber into the collection chamber, an electrical connection between to counter electrodes 34 and 35 placed in each chamber is established through the liquid. Cells are counted and differentiated by size by the Coulter principle. Through sizing of the cells, the cells can be distinguished and categorised into different groups containing cells of a certain type. Thus white blood cells (leucocytes) can be differentiated into granulocytes, lymphocytes and monocytes. Furthermore, thrombocytes (platelets) can be differentiated from leucocytes as well. In order to determine the concentration, the volume of the diluted blood, which has been counted, must be known. Since thrombocytes are approximately ten times as frequent as leucocytes, it may be necessary to measure two different volumes. The thrombocytes are counted according to a small volume chamber 6A positioned between the collection chamber and the larger volume. By registering the liquid entry and exit at the inlet and outlet of the small volume chamber respectively, the counting period will be given. Registration of the liquid level is preferably done by an optical reflectance measurement at the inlet 33 and at the outlet 32. The outlet of the small volume chamber is also the inlet of the large volume chamber 6B. This chamber is used in connection with counting of leucocytes. At the outlet of the large volume chamber, a third optical reflectance measurement 31 is performed to register the exit of the liquid from this chamber.

After counting both leucocytes and thrombocytes the haemoglobin content can be measured by optical spectroscopy preferably through the middle section of the large volume chamber 30.

Process of the test (example 6):

The process of making a test by means of the present invention can be characterized as:
1) Draw blood by using a lancet device
2) Pick up blood droplet by touching the blood to the cartridge inlet
3) Mount cartridge in the instrument (instrument starts and runs the test)
4) Read the result from the display
5) Remove and discard cartridge
FIG. 12

Example 7

Photolithography

An orifice may suitably be formed in a photo-reactive polymer by photolithography and subsequent development. Thus a free standing sheet of polymer of the kind used conventionally as a photo resist material may be exposed to light to render a spot to soluble to define an orifice (or to render the non-spot forming areas in-soluble) followed by development with solvent to remove material to form the orifice. Normally, a large number of count wafers each containing a respective orifice will be made simultaneously in one sheet. Suitable photo resist polymers are described in e.g. M. Madou "Fundamentals of Micro fabrication, CRC Press LLC, 1997, ISBN 0-8493-9451-1. They include AZ-5214E, SU8, polyamides and others.

Alternatively, the photo resist polymer may be used as a protecting layer over a substrate such as silicon in which the orifice is formed by etching regions exposed by development of the photo resist. If the etched substrate is electrically conducting it may be insulated prior to use by the formation of a suitable insulating layer there over. The photo resist polymer may be used as such a layer.

Count wafers made lithographically may be used in all forms of apparatus and method according to this invention. FIG. 12 shows one process of fabricating the count wafer: (a) appliance of a thin sheet of photo resist. (b) Development of the mask. (c) Etching of the orifice by Deep Reactive Ion Etching (DRIE, M. Madou "Fundamentals of Micro fabrication, CRC Press LLC, 1997, ISBN 0-8493-9451-1).
FIG. 13

Example 8

Orifice Fabricated by Laser Micro Machining

Orifices for Coulter counting can be fabricated by laser micro machining of polymers, which could lead to a simple and convenient way of fabricating and assembling orifices for the cartridge. A series of small holes of 50 µm has been fabricated with an UV-laser. The holes are made in less than 1 ms in a 50 µm polymer sheet. The uniformity of the holes is very high and the smoothness of the orifice entrance is unique. FIG. 13 shows the process of laser machining of the orifice. The laser cuts through the polymer foil in a circle, thus defining the size of the orifice.
FIG. 14

FIG. 14 shows schematically a preferred embodiment of the cartridge according to the invention. The illustrated cartridge has a first member 104 for sampling blood. The member 104 is movably positioned in relation to the housing between three positions, a first position for blood sampling, a second position to connect the first storage chamber 103 with the first mixing chamber 112, and a third position to connect the second storage chamber 105 with the second mixing chamber 110. The blood is passed through the bore 122 into the first cavity of the member 104 by capillary forces or by applying a vacuum at the end of the sampling channel 111. A liquid blocking valve 116 is arranged after the first sampling member to hinder passage of blood through the channel. After the blood sampling, the sampling member is turned to the second position and the sample is flushed into the first mixing chamber 112 by the liquid in the first storage chamber 103. In the first mixing chamber 112 the sample is diluted 1:200 with the liquid in the first storage chamber 103 and a fraction is blown back into the first cavity of the sampling member 104, which is turned to the third position so that the diluted sample is flushed into the second mixing chamber 110 by the liquid in the second storage chamber 105. In the second mixing chamber 110 the sample is further diluted 1:200 to a total dilution of 1:40.000 with the liquid in the second storage chamber 105. A hemolysing reagent is injected into the first mixing chamber 112 by a piston 115, which breaks a seal 118 between a reagent chamber 119 and the first mixing chamber 112. After hemolysing the blood the 1:200 diluted sample is ready for counting non-hemolysed white blood cells and for measuring hemoglobin by photometry. The white cells are counted by passing them through a first orifice 113 and measuring the response by impedance cell counting over a first electrode pair 117, 120. A fixed volume is counted by a first volume metering arrangement 107 connected to the first collection chamber 114. A first overflow volume 106 is arranged after the first volume metering arrangement 107. The white blood cells can be differentiated by volume after adding the lysing reagent to the blood. The white cells can be grouped by volume into: Granulocytes, Monocytes and Lymphocytes. The three groups together yield the total white cell count.

In the second mixing chamber 110, red cells and platelets are counted. The red cells and platelets are counted by passing them through a second orifice 109 and measuring the response by impedance cell counting over a second electrode pair 121, 125. A fixed volume is counted by a second volume metering arrangement 101 connected to the second collection chamber 108. A second overflow volume 102 is placed after the second volume metering arrangement 101.

The embodiment may further comprise an additional optical detector for photometric determination of the hemoglobin content. Referred to simply as "total hemoglobin", this test involves lysing the erythrocytes, thus producing an evenly distributed solution of hemoglobin in the sample. The hemoglobin is chemically converted to the more stable and easily measured methemoglobintriazole-complex, which is a colored compound that can be measured calorimetrically, its concentration being calculated from its amount of light absorption using Beer's Law. The method requires measurement of hemoglobin at approx. 540 nm where the absorption is high with a turbidity correction measurement at 880 nm where the absorption is low.

FIG. 15

FIG. 15 shows schematically another preferred embodiment of the cartridge according to the invention. The illustrated cartridge has a first member 104 for sampling blood. The member 104 is movably positioned in relation to the housing 100 between two positions, a first position for blood sampling, and a second position to connect the first storage chamber 103 with the first mixing chamber 112. A blood sample is passed through the bore 122 into the first cavity of the member 104 by capillary forces or by applying a vacuum at the end of the sampling channel 111. A liquid blocking valve 116 is arranged after the first sampling member to hinder passage of blood through the channel. After the blood sampling, the sampling member is turned to the second position and the sample is flushed into the first mixing chamber 112 by the liquid in the first storage chamber 103. In the first mixing chamber 112 the sample is diluted 1:200 with the liquid in the first storage chamber 103.

The cartridge further comprises a second sampling member 123 positioned in the housing 100 for sampling a small and precise volume of liquid from the first mixing chamber 112 and having a second cavity 123 for receiving and holding the sampled liquid, the member 123 being movably positioned in relation to the housing 100 in such a way that, in a first position, the second cavity 123 is in communication with the first mixing chamber 112 for entrance of a diluted sample from the first mixing chamber 112 into the second cavity 123, and, in a second position, the second cavity 123 is in communication with the second mixing chamber 110 so that the diluted sample is flushed into the second mixing chamber 110 by the liquid in the second storage chamber 105. In the second mixing chamber 110 the sample is further diluted 1:200 to a total dilution of 1:40.000 with the liquid in the second storage chamber 105. A hemolysing reagent is injected into the first mixing chamber 112 by a piston, which breaks a seal between a reagent chamber and the first mixing chamber 112. The piston, seal and reagent chamber are not shown in FIG. 15. After hemolysing the blood the 1:200 diluted sample is ready for counting non-hemolysed white blood cells and for measuring hemoglobin by photometry. The white cells are counted by passing them through a first orifice 113 and measuring the response by impedance cell counting over a first electrode pair 117, 120. A fixed volume is counted by a first volume metering arrangement 107 connected to the first collection chamber 114. A first overflow volume 106 is arranged after the first volume metering arrangement 107. The white blood cells can be differentiated by volume after adding the lysing reagent to the blood. The white cells can be grouped by volume into: Granulocytes, Monocytes and Lymphocytes. The three groups together yield the total white cell count.

In the second mixing chamber 110, red cells and platelets are counted. The red cells and platelets are counted by passing them through a second orifice 109 and measuring the response by impedance cell counting over a second electrode pair 121, 125. A fixed volume is counted by a second volume metering arrangement 101 connected to the second collection chamber 108. A second overflow volume 102 is placed after the second volume metering arrangement 101.

The embodiment may further comprise an additional optical detector for photometric determination of the hemoglobin content. Referred to simply as "total hemoglobin", this test involves lysing the erythrocytes, thus producing an evenly distributed solution of hemoglobin in the sample. The hemoglobin is chemically converted to the more stable and easily measured methemoglobintriazole-complex, which is a colored compound that can be measured calorimetrically, its concentration being calculated from its amount of light absorption using Beer's Law. The method requires measurement of hemoglobin at approx. 540 nm where the absorption is high with a turbidity correction measurement at 880 nm where the absorption is low.

The invention claimed is:

1. A cartridge for characterizing particles suspended in a liquid sample, comprising:
 a housing with connectors for operational connection to and disconnection from corresponding connectors of a docking station for establishment of electrical and fluid connections when the cartridge is received in the docking station,
 a first mixing chamber,
 a bore in an outer surface of the housing for entrance of the liquid sample,
 a first sampling member positioned in the housing for sampling the liquid sample and having a first cavity for receiving and holding the liquid sample, the first sampling member being movably positioned in relation to the housing in such a way that in a first position, the first cavity is in communication with the bore for entrance of the liquid sample into the first cavity, and in a second position the first cavity is in communication with the first mixing chamber for discharge of the liquid sample into the first mixing chamber whereby the sampling member operates to receive and hold a precise volume of the liquid sample and to transfer the liquid sample to the first mixing chamber, a first collection chamber separated by a first wall from the first mixing chamber, the first wall having a first orifice for the passage of particles directly from the first mixing chamber to the first collection chamber, and a first particle characterizer that characterizes the particles passing through the first orifice.

2. A cartridge according to claim 1, further comprising:

a second mixing chamber and a second collection chamber separated by a second wall containing a second orifice for the passage of the particles between the second mixing chamber and the second collection chamber, and a second particle characterizer that characterizes the particles passing through the second orifice, wherein when the first sampling member is in the second position, the first cavity is in communication with the first mixing chamber for entrance of the liquid sample from the first mixing chamber into the first cavity, and when the first sampling member is in a third position, the first cavity is in communication with the second mixing chamber for discharge of the liquid sample in the first cavity into the second mixing chamber.

3. A cartridge according to claim 1, further comprising:

a second mixing chamber and a second collection chamber separated by a second wall containing a second orifice for the passage of the particles between the second mixing chamber and the second collection chamber, a second particle characterizer that characterizes the particles passing through the second orifice, and a second sampling member positioned in the housing for sampling a small and precise volume of the liquid sample from the first mixing chamber and having a second cavity for receiving and holding the liquid sample, the second sampling member being movably positioned in relation to the housing in such a way that in a first position, the second cavity is in communication with the first mixing chamber for entrance of the liquid sample from the first mixing chamber into the first cavity, and in a second position the second cavity is in communication with the second mixing chamber for discharge of the liquid sample in the second cavity into the second mixing chamber.

4. A cartridge according to claim 1, further comprising a reagent chamber positioned adjacent to the first mixing chamber for holding a reagent to be entered into the first mixing chamber.

5. A cartridge according to claim 4, further comprising a breakable seal separating the reagent chamber from the first mixing chamber.

6. A cartridge according to claim 1, wherein the first particle characterizer includes a first electrode in the first mixing chamber and a second electrode in the first collection chamber, the first and second electrodes being electrically connected to respective terminal members accessible at the outer surface of the housing.

7. A cartridge according to claim 1, wherein the housing further comprises a liquid storage chamber for holding a liquid, the liquid storage chamber communicates with the first cavity when the first sampling member is in the second position so that liquid can be discharged from the liquid storage chamber through the first cavity of the first sampling member and into the first mixing chamber together with the liquid sample.

8. A cartridge according to claim 2, wherein the housing further comprises a liquid storage chamber for holding a liquid to be discharged from the liquid storage chamber through the first cavity and into the second mixing chamber together with the liquid sample.

9. A cartridge according to claim 1, comprising a volume meter that determines a beginning and an end of a period during which a predetermined volume of liquid has passed through the first orifice.

10. A cartridge according to claim 9, wherein the volume meter comprises a volume metering chamber with an input communicating with the first collection chamber, and an output, and wherein presence of liquid is detected by the volume meter at the input and at the output, respectively.

11. A cartridge according to claim 10, wherein presence of liquid is detected with an electrode positioned at the input and a further electrode positioned at the output.

12. A cartridge according to claim 10, wherein presence of liquid is detected optically.

13. A cartridge according to claim 1, wherein the first mixing chamber and the first collection chamber have transverse cross-sectional areas at a level of the first orifice, the transverse cross-sectional areas are substantially less than transverse cross-sectional areas of the first mixing chamber and the first collection chamber over a substantial part above the first orifice.

14. A cartridge according to claim 1, wherein a surface defining the first cavity of the first sampling member has an anti-coagulation reagent.

15. A cartridge according to claim 7, wherein the liquid storage chamber holds chemical reagents for modification of the liquid sample.

16. A cartridge according to claim 1, wherein a mixing member is positioned in the first mixing chamber.

17. A cartridge according to claim 16, wherein the mixing member is magnetic.

18. A cartridge according to claim 1, further comprising a sensor for characterization of the liquid sample.

19. A cartridge according to claim 18, wherein the sensor for characterization of the liquid sample is adapted for spectrophotometric characterization of the liquid sample.

20. A cartridge according to claim 1, wherein the housing further comprises a pump chamber communicating with the first collection chamber and having a pump actuator for causing liquid flow through the first orifice.

21. A cartridge according to claim 20, wherein the pump actuator is a piston.

22. A cartridge according to claim 20, wherein the pump actuator is a membrane.

23. A method of operating a particle characterization apparatus comprising a cartridge according to claim 7, the cartridge being demountable from the apparatus, the method comprising:

sampling liquid containing particles with the cartridge through the bore with the first sampling member in the first position, positioning the cartridge in the apparatus, moving the first sampling member to the second position, pumping liquid from the liquid storage chamber through the first cavity and into the first mixing chamber together with the liquid sample, making particle characterizing measurements, disconnecting the cartridge from the apparatus, and discarding the cartridge.

24. A method of operating a particle characterization apparatus comprising a cartridge according to claim 3, the cartridge being demountable from the apparatus and further comprising a first liquid storage chamber and a second liquid storage chamber for both holding liquid, the method comprising:
- sampling liquid containing particles with the cartridge through the bore with the first sampling member in the first position,
- positioning the cartridge in the apparatus,
- moving the first sampling member to the second position,
- pumping liquid from the first liquid storage chamber through the first cavity and into the first mixing chamber together with the liquid sample,
- sampling a liquid sample from the first mixing chamber with the second sampling member in the first position,
- moving the second sampling member to the second position,
- pumping liquid from the second liquid storage chamber through the second cavity and into the second mixing chamber together with the liquid sample,
- making particle characterizing measurements with the first and second particle characterizers,
- disconnecting the cartridge from the apparatus, and
- discarding the cartridge.

25. An apparatus for characterizing particles suspended in a liquid, comprising:
a cartridge according to claim 1, and
a docking station for removably receiving the cartridge, comprising connectors for operational connection with the first particle characterizer when the cartridge is received in the docking station.

26. An apparatus according to claim 25, wherein the cartridge further comprises a first port communicating with the first collection chamber for causing liquid flow through the first orifice, and
the docking station further comprises a port for forming a gas connection with the first port when the cartridge is received in the docking station for application of a pressure causing a liquid flow through the orifice.

27. A cartridge according to claim 3, wherein the second particle characterizer includes a first electrode in the second mixing chamber and a second electrode in the second collection chamber, the first and second electrodes being electrically connected to respective terminal members accessible at the outer surface of the housing.

28. A cartridge according to claim 3, wherein the housing further comprises a liquid storage chamber for holding a liquid to be discharged from the liquid storage chamber through the second cavity and into the second mixing chamber together with the liquid sample.

29. A cartridge according to claim 2, comprising a volume meter that determines a beginning and an end of a period during which a predetermined volume of liquid has passed through the second orifice.

30. A cartridge according to claim 3, comprising a volume meter that determines a beginning and an end of a period during which a predetermined volume of liquid has passed through the second orifice.

31. An apparatus for characterizing particles suspended in a liquid, comprising:
a cartridge according to claim 2, and
a docking station for removably receiving the cartridge, comprising connectors for operational connection with the first particle characterizer and the second particle characterizer when the cartridge is received in the docking station.

32. An apparatus according to claim 3, wherein the cartridge further comprises a first port communicating with the first collection chamber for causing liquid flow through the first orifice, and a second port communicating with the second collection chamber for causing liquid flow through the second orifice, and
the docking station further comprises a first port and a second port for forming a gas connection with the first port and the second port of the cartridge when the cartridge is received in the docking station for application of a pressure causing liquid flow through the first orifice and the second orifice.

33. An apparatus for characterizing particles suspended in a liquid, comprising:
a cartridge according to claim 3, and
a docking station for removably receiving the cartridge, comprising connectors for operational connection with the first particle characterizer and the second particle characterizer when the cartridge is received in the docking station.

34. A cartridge for characterizing particles suspended in a liquid sample, comprising:
- a housing with connectors for operational connection to and disconnection from corresponding connectors of a docking station for establishment of electrical and fluid connections when the cartridge is received in the docking station,
- a first mixing chamber,
- a bore in an outer surface of the housing for entrance of the liquid sample,
- a first movable sampling member positioned in the housing for sampling the liquid sample and having a first cavity for receiving and holding a precise volume of the liquid sample, and for discharging the held liquid sample into the first mixing chamber,
- a first collection chamber separated by a first wall from the first mixing chamber, the first wall having a first orifice for the passage of particles directly from the first mixing chamber to the first collection chamber, and
- a first particle characterizer that characterizes the particles passing directly from the first mixing chamber to the first collection chamber through the first orifice.

35. The cartridge according to claim 34, wherein the first particle characterizer includes a first electrode in the first mixing chamber and a second electrode in the first collection chamber.

* * * * *